US012797380B2

(12) United States Patent
Jain et al.

(10) Patent No.: US 12,797,380 B2
(45) Date of Patent: Nov. 17, 2026

(54) TREATMENT OF SICKLE CELL ANAEMIA

(71) Applicant: ZYDUS LIFESCIENCES LIMITED, Ahmedabad (IN)

(72) Inventors: Mukul Jain, Ahmedabad (IN); Amit Joharapurkar, Ahmedabad (IN); Vishal Patel, Ahmedabad (IN)

(73) Assignee: ZYDUS LIFESCIENCES LIMITED, Ahmedabad (IN)

( * ) Notice: Subject to any disclaimer, the term of this patent is extended or adjusted under 35 U.S.C. 154(b) by 393 days.

(21) Appl. No.: 18/551,214

(22) PCT Filed: Mar. 17, 2022

(86) PCT No.: PCT/IB2022/052429
§ 371 (c)(1),
(2) Date: Sep. 19, 2023

(87) PCT Pub. No.: WO2022/195532
PCT Pub. Date: Sep. 22, 2022

(65) Prior Publication Data
US 2024/0173314 A1 May 30, 2024

(30) Foreign Application Priority Data
Mar. 19, 2021 (IN) ............................ 202121011754

(51) Int. Cl.
*A61K 31/4704* (2006.01)
*A61K 45/06* (2006.01)
*A61P 7/06* (2006.01)

(52) U.S. Cl.
CPC .......... *A61K 31/4704* (2013.01); *A61K 45/06* (2013.01); *A61P 7/06* (2018.01)

(58) Field of Classification Search
CPC .............................. A61K 31/4704; A61P 7/06
USPC ......................................................... 514/312
See application file for complete search history.

(56) References Cited

U.S. PATENT DOCUMENTS

| | | | | |
|---|---|---|---|---|
| 8,598,210 | B2 | 12/2013 | Kawamoto et al. | |
| 9,394,300 | B2 * | 7/2016 | Desai | A61P 7/06 |
| 2019/0359574 | A1 | 11/2019 | Desai et al. | |

FOREIGN PATENT DOCUMENTS

| | | | | |
|---|---|---|---|---|
| WO | 2014102818 A1 | 7/2014 | | |
| WO | 2019028150 A1 | 2/2019 | | |
| WO | WO 2021/18360 A1 * | 9/2021 | C07D 215/00 | |
| WO | WO 2022/150623 A1 * | 7/2022 | | |

OTHER PUBLICATIONS

International Search Report for PCT/IB2022/052429 dated Jun. 21, 2022 (4 pages).

Griffiths, C. E. M. et al., www.thelancet.com, vol. 370 Jul. 21, 2007, pp. 263-271.

Tesmer , L. A. et al., Th17 cells in human disease, Immunological Reviews 223/2008, pp. 87-113.

Helliwell, P.S., Classification and diagnostic criteria for psoriatic arthritis, Ann Rheum Dis 2005;64(Suppl II):ii3-ii8.

Dang E. V et al., Control of TH17/Treg Balance by Hypoxia-Inducible Factor 1, Cell 146, 772-784, Sep. 2, 2011, pp. 772-794.

McNamee E. N. et al., Hypoxia and hypoxia-inducible factors as regulators of T cell development, differentiation, and function, Immunol Res (2013) 55, pp. 58-70.

Walmsley, S. R. et al., Hypoxia-induced neutrophil survival is mediated by HIF-1a-dependent NF-kB activity, JEM, vol. 201, No. 1, Jan. 3, 2005, pp. 105-115.

Albina, J. E. et al., HIF-1 expression in healing wounds: HIF-1a induction in primary inflammatory cells by TNF-a, Am J Physiol Cell Physiol 281: C1971-C1977, 2001.

Blouin, C.C. et al., Hypoxic gene activation by lipopolysaccharide in macrophages:implication of hypoxia-inducible factor 1a, Blood, 2004, V103, No. 3, pp. 1124-1130.

Fitzpatrick, S. F. et al., An Intact Canonical NF-kB Pathway Is Required for Inflammatory Gene Expression in Response to Hypoxia, J Immunol, 2011, 186: pp. 1091-1096.

Scholz, C. C. et al., Regulation of IL-1B-induced NF-κB by hydroxylases links key hypoxic and inflammatory signaling pathways, PNAS, 2013, vol. 110, No. 46: pp. 18490-18495.

Robinson, A. R. et al., Mucosal Protection by Hypoxia-Inducible Factor Prolyl Hydroxylase Inhibition, Gastroenterology 2008, 134:pp. 145-155.

Tambuwala, M.M. et al., Loss of Prolyl Hydroxylase-1 Protects Against Colitis Through Reduced Epithelial Cell Apoptosis and Increased Barrier Function, Gastroenterology, 2010, 139: pp. 2093-2101.

Manresa, M. et al., Pharmacologic inhibition of hypoxia inducible factor (HIF)-hydroxylases ameliorates allergic contact dermatitis, Allergy, 2019, 74: pp. 753-766.

(Continued)

*Primary Examiner* — Charanjit Aulakh
(74) *Attorney, Agent, or Firm* — Renner, Kenner, Greive, Bobak, Taylor & Weber Co. LPA

(57) ABSTRACT

Present invention relates to development of compound of formula (Ia) for treatment of sickle cell anaemia. Invention also relates to the pharmaceutical composition comprising compound of formula (Ia) or its pharmaceutically acceptable salts for treatment of sickle cell anaemia.

formula (Ia)

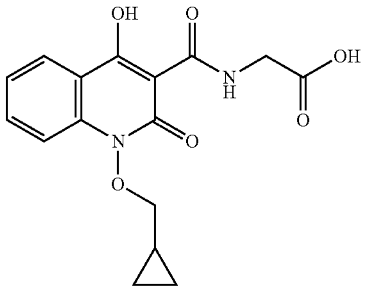

18 Claims, 3 Drawing Sheets

(56) References Cited

OTHER PUBLICATIONS

Jain, M. et al., Pharmacological inhibition of prolyl hydroxylase protects against inflammationinduced anemia via efficient erythropoiesis and hepcidin downregulation, European Journal of Pharmacology, Accepted Manuscript, https://doi.org/10.1016/j.ejphar.2018.11.023.

Joharapurkar, A.A. et al., Prolyl Hydroxylase Inhibitors: A Breakthrough in the Therapy of Anemia Associated with Chronic Diseases, J. Med. Chem. 2018, 61, pp. 6964-6982.

Patel, V.J. et al., Coagonist of glucagon-like peptide-1 and glucagon receptors ameliorates kidney injury in murine models of obesity and diabetes mellitus, World J Diabetes, 2018, 9(6): pp. 80-91.

Joharapurkar, A.A., et al., Prolyl hydroxylase inhibitor desidustat protects against acute and chronic kidney injury by reducing inflammatory cytokines and oxidative stress, Drug Dev Res. 2021, pp. 1-9.

* cited by examiner

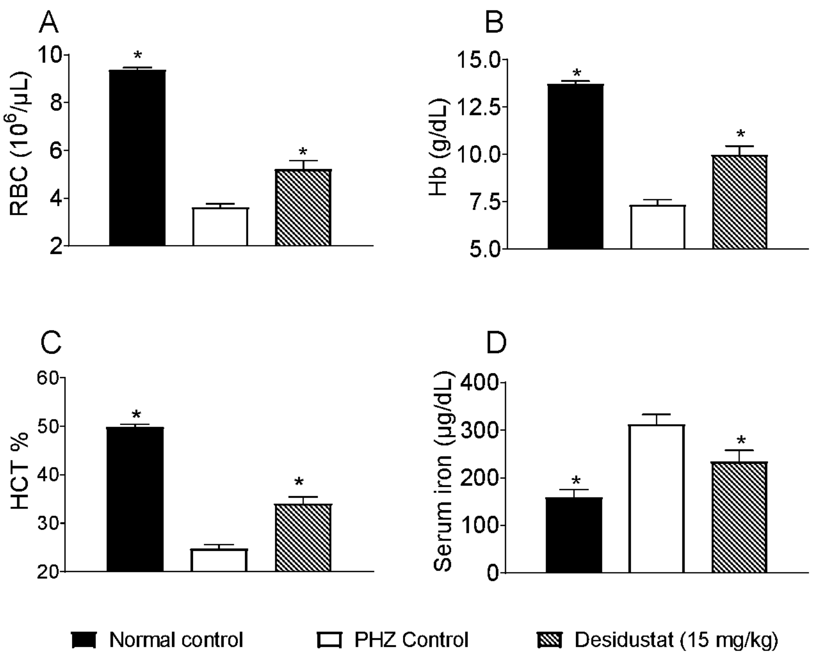
Figure 1: The effect of compound of formula (Ia) on PHZ-induced haemolytic anaemia in mice.

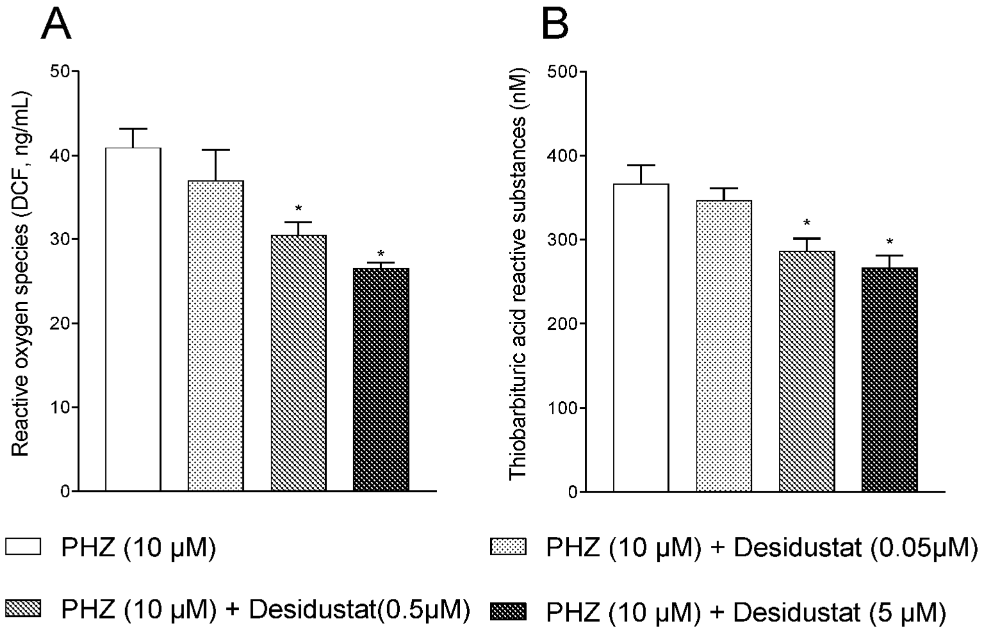
Figure 2: The effect of compound of formula (Ia) on PHZ-induced oxidative stress in isolated RBC.

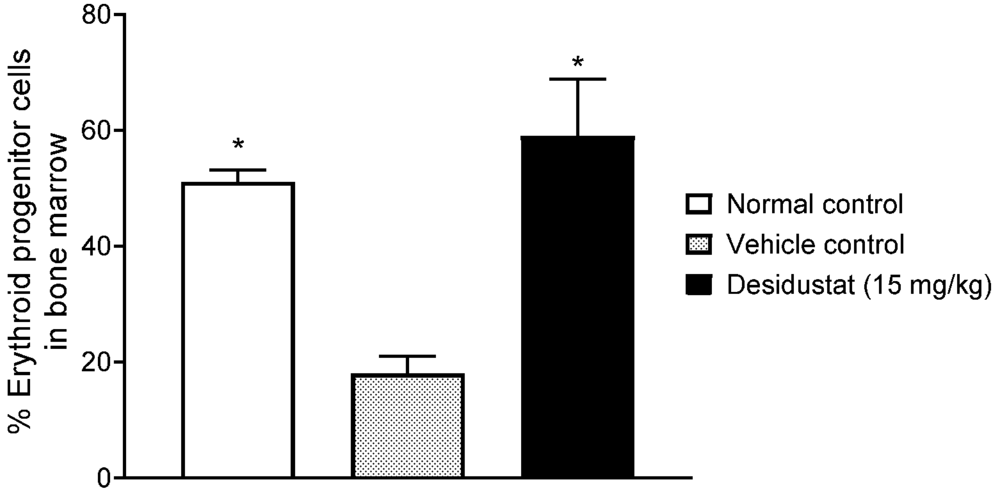
Figure 3: The effect of compound of formula (Ia) on % erythroid progenitor cells in bone marrow of anemic rats.

TREATMENT OF SICKLE CELL ANAEMIA

FIELD OF THE INVENTION

Present invention relates to the development of therapeutic compound for the treatment of sickle cell anaemia. Specifically, present invention relates to compound of formula (Ia) or its pharmaceutically acceptable salt or pharmaceutical composition thereof useful for the treatment of sickle cell anaemia.

BACKGROUND OF THE INVENTION

Anaemia is a condition in which a patient has lack of healthy red blood cells in body to carry out adequate oxygen to body. Anaemia is commonly classified on the basis of its cause or deficiency such as iron deficiency anaemia, vitamin deficiency anaemia, sickle cell anaemia, or anaemia due to some specific medical treatments (e.g. chemotherapy) etc. Out of these, anaemia caused by any deficiency or due to any medical treatment is comparatively easy to treat but there are very limited treatments available for anaemia such as sickle cell anaemia and other rare type of hemoglobin disorders. There is always need of better treatment in this area of sickle cell anaemia and other such disorders to provide a new drug composition with improved efficacy.

Specifically, sickle cell disease (SCD) or sickle cell anaemia is a lifelong inherited disorder affecting integrity of red blood cell (RBC). In sickle cell disease, RBC becomes crescent or "sickle" shaped, which are disc shaped normally. These occurs because of presence of two abnormal copy of β-globin gene (gene responsible for Hb synthesis). Low oxygen tension promotes sickling of RBC and damage the cell membrane and decrease the cell's elasticity. SCD has various acute and chronic complications having high mortality rate. Due to destruction of sickled red blood cells (RBC), these is an occurrence of acute anaemia. The average life span of sickled RBC is about 10-20 days, which is 120 days for normal RBC. The bone marrow fails to compensate the rate of destruction and leads to chronic anaemia. As sickled RBC are rigid than normal RBC, they cannot pass through narrow capillary and thus occlude the flow leading to ischemia. A number of consequences develops in SCD such as delay in growth, swelling in the hands and feet, bacterial infections, stroke, cholelithiasis, leg ulcers, pulmonary hypertension, cardiac diseases, and chronic kidney failure.

Sickle cell disease generates a state of high oxidative burden which disturbs redox homeostasis of the body, due to excessive levels of free hemoglobin, and recurrent ischemia. Higher auto-oxidation of abnormal hemoglobin (HbS) generates superoxide radicals and hence hydrogen peroxide. Increased serum lactate dehydrogenase and bilirubin were also observed in SCD. Chronic proinflammatory response in SCD cause infiltration of neutrophils and monocytes, which secrete inflammatory mediators (Queiroz et al., 2013). The current treatment options for SCD are hydroxyurea, transfusion, L-glutamine, crizanlizumab, and voxelotor (Fiocchi J et al., 2020; Telen M J 2020). Other options for care of SCD are blood transfusion and bone marrow transplantation.

Oxygen is an important factor which regulates acute and chronic inflammation. Oxygen levels in the tissues are sensed by hypoxia-inducible factors (HIFs: HIF-1 and HIF-2), regulated by prolylhydroxylase enzymes (Joharapurkar et al., 2018). Inhibition of PHD can stabilize HIF thus increasing the availability of HIF at the site of inflammation. Hypoxia inducible factor (HIF) regulates erythropoietin (EPO) secretion and inhibition of PHD thus increases EPO by stabilizing HIF. HIF is involved in increased production of fetal hemoglobin (HbF). It has been observed that EPO in combination with hydroxyurea, showed further increase in HbF than alone hydroxyurea (Rodgers G P et al., 1993). Stabilization of HIF by PHD inhibitor also increases HbF from human bone marrow cells (Hsieh M M et al., 2007). Apart from these, HIF has been reported to regulate nuclear factor-κB (NF-κB) and extracellular signal-regulated kinase (ERK) mediated inflammatory pathways (Scholz et al., 2013). Stabilization of HIF exerts anti-inflammatory effect (Biddlestone J et al., 2015; Hirai K et al., 2018). Desidustat is a PHD inhibitor recently approved drug in India for treatment of anaemia in chronic kidney disease. It is reported that desidustat treatment stabilizes HIF and thus induces erythropoiesis in animal model of anaemia (Jain et al., 2019; Joharapurkar et al., 2018). Desidustat treatment reduced IL-6 and IL-1β levels in ischemia condition (Joharapurkar et al., 2021). These inflammatory markers were increased in SCD. It also decreases superoxide dismutase (SOD) and malondialdehyde (MDA) thus decreases oxidative stress (Joharapurkar et al., 2021). SCD has increased iron overload, and has increased levels of hepcidin (Omena J et al., 2018). Scientists have surprisingly found that compound of formula (Ia) also works well in increasing erythroid progenitor cells in bone marrow.

Some of the prolyl hydroxylase inhibitors have been disclosed in EP 661269, WO 2007070359, WO 2008076425, WO 2011007856, WO 2012106472, WO 2013043621, WO 2004108681 and WO 2008002576 covers the prolyl hydroxylase inhibitors. Pharmaceutical composition for treatment of oxidative stress disorders and treatment of hemoglobin disorders have been disclosed in WIPO publications WO 2014200773, WO 2017027810 and WO 2019028150 respectively.

WO 2014102818 discloses compounds of the following general formula (I)

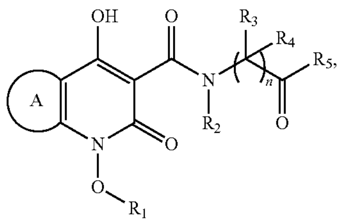

the compound of formula (Ia) as given below formula (Ia)

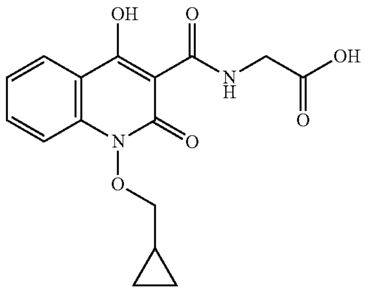

and its pharmaceutically acceptable salts are found effective in the treatment of sickle cell anaemia. U.S. Pat. No. 10,899,713 discloses process for the preparation of compound of formula (Ia).

Objectives of the Invention

In an embodiment, the present invention provides a compound of formula (Ia) or its pharmaceutically acceptable salts suitable for the treatment of sickle cell anaemia.

In another embodiment, the present invention provides pharmaceutical composition comprising compound of formula (Ia) or its pharmaceutically acceptable salts and pharmaceutically acceptable excipients for treatment of sickle cell anaemia.

In another embodiment, the present invention provides a method of treating sickle cell anaemia using pharmaceutical composition of compound of formula (Ia) or its pharmaceutically acceptable salts.

In another embodiment, the present invention provides the administration of compound of formula (Ia), its pharmaceutically acceptable salts or pharmaceutical composition thereof alone or in combination with other suitable therapeutic agent for the treatment of sickle cell anaemia.

SUMMARY OF THE INVENTION

Present invention relates to compound of formula (Ia) or its pharmaceutically acceptable salts for the treatment of sickle cell anaemia. Invention also relates to pharmaceutical composition comprising compound of formula (Ia) or pharmaceutically acceptable excipients useful for the treatment of sickle cell anaemia.

DESCRIPTION OF FIGURES

FIG. 1: The effect of compound of formula (Ia) on PHZ-induced haemolytic anaemia in mice.

FIG. 2: The effect of compound of formula (Ia) on PHZ-induced oxidative stress in isolated RBCs.

FIG. 3: The effect of compound of formula (Ia) on % erythroid progenitor cells in bone marrow of anemic rats.

DESCRIPTION OF THE INVENTION

Definition

The terms 'treatment' or 'treat' refer to slowing, stopping, or delaying the progression of the disease or clinical symptoms in a patient, as evidenced by a decrease or elimination of a clinical or diagnostic symptom of the disease, disorder or condition.

The term 'subject' refer to a mammals.

The term 'effective amount' in the context of the administration of the amount of the drug substance sufficient to have the desired effect.

The term 'pharmaceutically acceptable' use embraces both human and veterinary use.

In an embodiment, present invention provides a compound of formula (Ia) or its pharmaceutically acceptable salts suitable for the treatment of sickle cell anaemia.

formula (Ia)

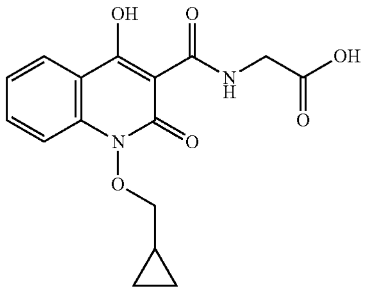

Pharmaceutically acceptable salts of compound of formula (Ia) are cations, may be selected from metal ions, amine bases and amino acids.

Wherein metal may be selected from calcium, sodium, potassium, lithium, barium, strontium, magnesium, cesium, copper, cobalt, iron, manganese, lead, aluminum, cadmium, silver, zinc, ammonium and the like; amine base may be selected from methylamine, dimethylamine, ethylamine, diethyl amine, n-propyl amine, isopropyl amine, diisopropyl amine, N-methyl isopropyl amine, n-butyl amine, t-butyl amine, 2-butamine, 1,2-ethane diamine, N-methylglucamine, N,N,N-trimethyl ethanolamine hydroxide (choline), tromethamine, cyclohexylamine, N-methyl cyclohexylamine, guanidine, N-(4-aminobutyl) guanidine, dicyclohexylamine, benzene-methanamine, ethanolamine, diethanolamine, tris-(hydroxymethyl)methylamine, hydroxylamine, methanaminium, benzylamine, N-methylbenzylamine, N-ethyl benzylamine, 4-methoxybenzylamine, pyrrolidine, piperidine, piperazine, morpholine, 2-aminopyrimidine, 2-thiopheneethanamine, (2S)-3,3-dimethyl-2-butanamine, cyclopentanamine, cycloheptanamine, meglumine, benethamine, dibenzylamine, diphenylamine, α-naphthylamine, α-phenylenediamine, O-Diaminopropane, (S)-α-naphthylethylamine, (S)-3-methoxyphenylethylamine, (S)-4-methoxyphenylethylamine, (S)-4-chlorophenylethylamine, (S)-4-methylphenylethylamine, cinchonine, cinchonidine, (-)-quinine, triethanolamine, imidazole, ethylenediamine, epolamine, morpholine 4-(2-hydroxyethyl), N—N-diethylethanolamine, deanol, hydrab amine, betaine, adamantanamine, L-adamantanmethylamine, tritylamine, gluc amine, N-methyl pyrrolidine, urea, procaine, metformin, hexane-1,6-diamine, 2-(2-aminoethoxy)ethanamine, N-methylmorpholine, and N-ethylmorpholine; amino acid may be selected from alanine, lysine, arginine, histidine, threonine, proline, glutamine and glycine.

In an embodiment, the present invention provides effective amount of compound of formula (Ia) or its pharmaceutically acceptable salt may be selected from 1 mg to 500 mg; preferably 1 mg to 250 mg and more preferably 4 mg to 50 mg for the treatment of sickle cell anaemia.

In an embodiment, the present invention provides effective amount of compound of formula (Ia) or its pharmaceutically acceptable salt may be administered by oral, topical, parenteral, intravenous or intramuscular route of administration. In a preferred embodiment, the present invention provides effective amount of formula (Ia) or its pharmaceutically acceptable salt is administered by oral route of administration.

The compound of formula (Ia) or its pharmaceutically acceptable salts may be provided to the subject daily, weekly, as prescribed by physician to the person in need thereof.

In an embodiment, the present invention provides the combination of compound of formula (Ia) and their pharmaceutically acceptable salts with other suitable agents as therapeutic agent for the treatment of sickle cell anaemia.

Wherein other suitable therapeutic agents may be selected from prolyl hydroxylase inhibitors such as Roxadustat, Molidustat, Daprodustat and the like. Some other drug such as hydroxyurea, crizanluzumab, voxelotor, L-glutamine, NSAIDs may also be used in combination with compound of formula (Ia) for treatment of sickle cell anaemia.

In yet another embodiment, compound of formula (Ia) is provided in the form of pharmaceutical composition. Wherein composition further comprising pharmaceutically acceptable excipients selected from disintegrating agents, diluents, binders, lubricating agents, glidant agents, coating redimix and the like.

In an embodiment, present invention provides a pharmaceutical composition comprising compound of formula (Ia) or its pharmaceutically acceptable salts for treatment of sickle cell anaemia wherein compound of formula (Ia) is formula (Ia)

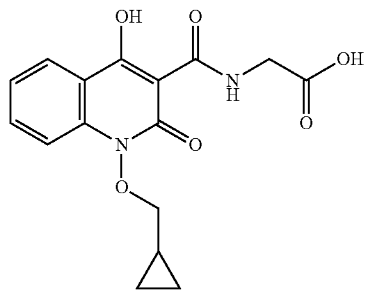

Pharmaceutical acceptable salts of the compound of formula (Ia) wherein cation may be selected from metal, amine bases and amino acids.

Wherein metal may be selected from calcium, sodium, potassium, lithium, barium, strontium, magnesium, cesium, copper, cobalt, iron, manganese, lead, aluminum, cadmium, silver, zinc, ammonium and the like; amine base may be selected from methylamine, dimethylamine, ethylamine, diethyl amine, n-propyl amine, isopropyl amine, diisopropyl amine, N-methyl isopropyl amine, n-butyl amine, t-butyl amine, 2-butamine, 1,2-ethane diamine, N-methylglucamine, N,N,N-trimethyl ethanolamine hydroxide (choline), tromethamine, cyclohexylamine, N-methyl cyclohexylamine, guanidine, N-(4-aminobutyl) guanidine, dicyclohexylamine, benzene-methanamine, ethanolamine, diethanolamine, tris-(hydroxymethyl)methylamine, hydroxylamine, methanaminium, benzylamine, N-methylbenzylamine, N-ethyl benzylamine, 4-methoxybenzylamine, pyrrolidine, piperidine, piperazine, morpholine, 2-aminopyrimidine, 2-thiopheneethanamine, (2S)-3,3-dimethyl-2-butanamine, cyclopentanamine, cycloheptanamine, meglumine, benethamine, dibenzylamine, diphenylamine, α-naphthylamine, O-phenylenediamine, 1,3-Diaminopropane, (S)-α-naphthylethylamine, (S)-3-methoxyphenylethylamine, (S)-4-methoxyphenylethylamine, (S)-4-chlorophenylethylamine, (S)-4-methylphenylethylamine, cinchonine, cinchonidine, (-)-quinine, triethanolamine, imidazole, ethylenediamine, epolamine, morpholine 4-(2-hydroxyethyl), N—N-diethylethanolamine, deanol, hydrabamine, betaine, adamantanamine, L-adamantanmethylamine, tritylamine, glucamine, N-methyl pyrrolidine, urea, procaine, metformin, hexane-1,6-diamine, 2-(2-aminoethoxy)ethanamine, N-methylmorpholine, and N-ethylmorpholine; amino acid may be selected from alanine, lysine, arginine, histidine, threonine, proline, glutamine and glycine.

In an embodiment, the present invention provides pharmaceutical composition comprising compound of formula (Ia) and suitable pharmaceutically acceptable excipients for the treatment of sickle cell anaemia.

In a preferred embodiment, the present invention provides a pharmaceutical composition comprising compound of formula (Ia), a suitable disintegrating agent and other pharmaceutically acceptable excipients for treatment of sickle cell anaemia.

In an embodiment, a suitable disintegrating agent may be selected from maize starch, sodium starch glycolate, crospovidone, and suitable combination thereof.

In an embodiment, the present invention provides a pharmaceutical composition comprising compound of formula (Ia) or its pharmaceutically acceptable salts wherein effective amount of compound of formula (Ia) or its pharmaceutically acceptable salt may be selected from 1 mg to 500 mg; preferably 1 mg to 250 mg and more preferably 4 mg to 50 mg for the treatment of sickle cell anaemia.

In an embodiment, the present invention provides pharmaceutical composition comprising compound of formula (Ia) or its pharmaceutically acceptable salt may be administered by oral, topical, parenteral, intravenous or intramuscular route of administration. In a preferred embodiment, the pharmaceutical composition may be administered by oral route of administration.

The pharmaceutically acceptable excipients may be selected at least one from diluent, binder, lubricating agent, glidant agent, coating redimix and the like.

Diluent include, but are not limited to lactose monohydrate, lactose, microcrystalline cellulose, polymethacrylates selected from Eudragit, potassium chloride, sulfobutylether b-cyclodextrin, sodium chloride, mannitol, compressible sugars, hydroxylpropyl cellulose, magnesium carbonate, calcium carbonate, maltitol, lactitol, sorbitol, sugar alcohol, magnesium oxide, calcium silicate, spray dried lactose, and suitable combinations thereof and other such materials known to those of ordinary skill in the art.

Binders include, but are not limited to hypromellose 3 Cps, carbomers, cellulose derivatives such as cellulose acetate phthalate, carbopol, gellan, chitosan, hydrogenated vegetable oil, sodium algenate, povidone, sugar, hydroxypropylmethyl-cellulose, hydroxypropyl cellulose, starch, alginic acid, acacia, pre-gelatinized starch, tragacanth, eudragit, xanthan gum, polymethacrylates and suitable combination thereof and other such materials known to those of ordinary skill in the art. In one of the embodiment, binders may selected from povidone, sodium alginate, hydroxypropyl cellulose, hydroxypropylmethyl cellulose, starch and suitable combination thereof.

Glidant agent include, but are not limited to, colloidal silica, fumed silica, calcium silicate, magnesium silicate, silicon hydrogel, cornstarch, talc, bentonite and suitable combinations thereof and other such materials known to those of ordinary skill in the art. In one embodiment, glidants may selected from calcium silicate, magnesium silicate, silicon hydrogel, corn starch and suitable combination thereof.

Lubricating agent include, but are not limited to, calcium stearate, magnesium stearate, mineral oil, stearic acid, silica, zinc stearate, glycerin behenate, vegetable oil, hydrogenated vegetable oil, castor oil, hydrogenated castor oil, fats, sodium stearyl fumarate, talc and fatty acids including myristic acid, oleic acid, lauric acid, oleic acid, derivatives of polyethylene glycol, glyceryl monostearate and suitable combinations thereof and other such materials known to those of ordinary skill in the art. In one of the embodiment, lubricant may be selected from stearic acid, zinc stearate, castor oil, hydrogenated castor oil, sodium steryl fumarate, fatty acids, glyceryl monostearate and derivatives of polyethylene glycol and suitable combination thereof.

Coating redimix is selected from Opadry Pink all such materials known to those of ordinary skill in the art.

In an embodiment, the present invention provides the pharmaceutical composition comprising compound of formula (Ia), its pharmaceutically acceptable salts and optionally other suitable therapeutic agents for treatment of sickle cell anaemia.

In an embodiment other suitable therapeutic agent may be selected from prolyl hydroxylase inhibitors such as Roxadustat, Molidustat, Daprodustat and the like; some other drugs such as hydroxyurea, crizanluzumab, voxelotor, L-glutamine, NSAIDs may also use in combination with compound of formula (Ia) for treatment of sickle cell anaemia.

In another embodiment, the present invention provides a method of treating sickle cell anaemia using pharmaceutical composition of compound of formula (Ia) or its pharmaceutically acceptable salts. In a preferred embodiment, a method of treating sickle cell anaemia using compound of formula (Ia) or its pharmaceutical composition.

The criteria of treatment such as dosing amount, dosing schedule and duration of treatment is to be decided by the medical practitioner or physician as per the need of the subject or a person in need thereof. The medical practitioner may prescribe pharmaceutical composition comprising compound of formula (Ia) in combination in combination of other drugs or along with another therapy.

EXAMPLE

Study Design and Treatment

Effect of Compound of Formula (Ia) Treatment in Phenylhydrazine-Induced Anemia Male C57BL/6J (6-8 weeks old) were used in the study. Mice were treated with phenylhydrazine (PHZ) on day 0, day 1 and day 3. The PHZ was given by intraperitoneally route at 40 mg/kg on day 0, and 20 mg/kg on day 1 and 3. Vehicle control or compound of formula (Ia) (15 mg/kg, PO) was given daily from day −1 to day 5. At the end of treatment period, whole blood samples were processed for haemoglobin, RBC and haematocrit measurement. The serum samples were analyzed for total iron content. The effect on oxidative and inflammatory markers will be analyzed.

Effect of Compound of Formula (Ia) on Reactive Oxygen Species and TBARS in RBC The RBC was isolated from healthy male C57BL/6J (6-8 weeks old) into a heparinized tube. The RBC pellet was isolated by centrifugation. The RBC pellet was washed three time with glucose supplemented phosphate buffered saline (PBS). The final RBC pellet was diluted 1:4 with glucose supplemented PBS. The RBC suspension was incubated with compound of formula (Ia) at 0.05, 0.5 and 5 μM concentration for 30 min at 37 °C. Then the phenylhydrazine (10 μM) was added to all groups and incubated for further 30 min at 37 °C. After that 2,7-Dichlorofluorescin-diacetate (DCFDA, 400 μM) was added to the RBC suspension and incubated for 30 min at 37 °C. After incubation, the RBC suspension was washed two times with glucose-PBS, and RBC were lysed with 200 μL of ice-cold 0.1% Triton X100 and then incubated for 30 min in darkness at room temperature. After 30 min incubation, the fluorescence of all samples was read (excitation wavelength: 485 nm and emission wavelength: 538 nm). The concentration of 2,7-Dichlorofluorescin (DCF) was calculated from the DCF standard curve. For thiobarbituric acid reactive substances (TBARS) measurement, RBC lysate was used and malondialdehyde was measured using thiobarbituric acid method (Patel V et al., 2018).

Effect of Compound of Formula (Ia) on Production of Erythroid Progenitor Cells in Anemic Rats The anaemia was induced by cisplatin (5 mg/kg, IP, single dose) and turpentine oil (5 mL/kg, SC, twice a week) administration for four weeks. The compound of formula (Ia) (15 mg/kg, PO, alternate day) treatment was initiated after two weeks of cisplatin/turpentine oil administration. After two weeks of compound of formula (Ia) treatment, animals were euthanized and bone marrow was isolated. Bone marrow smear was prepared and stain with May-Grunwald stain and Giemsa stain. The ratio of erythroid progenitor cell: total cells were expressed as percentage.

Effect of Compound of Formula (Ia) Treatment on Sickling, Fragility and Oxidative Stress in RBC of Sickle Cell Disease Patients Whole blood will be collected from sickle cell disease patients. RBCs isolated by centrifugation and washed with isotonic saline. The fragility of RBC will be checked by suspending RBC suspension in 0.00 to 0.9% of buffered saline at pH of 7.4 in presence or absence of compound of formulat (Ia) at 0.1 nM to 10 mM concentration. The mixture will be incubated at 37 °C for 2-24 h. The mixture will be centrifuged and optical density of the supernatant will be read at 540 nm. The % of saline at which 50% fragility occurs will be calculated.

The polymerization of RBC will be assessed in presence of sodium metabisulphite. The isolated RBC will be incubated with 2% sodium metabisulphite solution in presence or absence of compound of formula (Ia) at 0.1 nM to 10 mM concentration at 37 °C for 2-24 h. The sickling of RBC will be analyzed microscopically. Percentage of sickling will be calculated.

For measurement of oxidative stress, isolated RBC will be incubated with $H_2O_2$ or Then the phenylhydrazine in presence or absence of compound of formula (Ia) at 0.1 nM to 10 mM concentration at 37 °C for 30 min. After that 2,7-Dichlorofluorescin-diacetate (DCFDA, 400 μM) added to the RBC suspension and incubated for 30 min at 37 °C. RBC will be lysed after washing and then incubated for 30 min in dark at room temperature. The fluorescence of all samples will be read (excitation wavelength: 485 nm and emission wavelength: 538 nm). The concentration of 2,7-Dichlorofluorescin (DCF) will be calculated from the DCF standard curve.

For measurement of inflammation, whole blood from sickle cell patients will be incubated in presence or absence of compound of formula (Ia) at 0.1 nM to 10 mM concentration at 37 °C for 2-24 h. The levels of inflammatory mediators will be assessed in the supernatant to measure markers of vasculopathy and hemolysis.

Effect of Compound of Formula (Ia) Treatment on Vascular Inflammation

The isolated peritoneal macrophages from mice and human white blood cells (isolated from whole blood) will be incubated overnight presence or absence of compound of formula (Ia) at 0.1 nM to 10 mM concentration at 37 °C. The incubated cell suspension will be centrifuged and levels of the inflammatory mediators will be analyzed.

Results

Effect of Compound of Formula (Ia) Treatment in Phenylhydrazine-Induced Anaemia

PHZ treatment decreased RBC, hemoglobin and HCT levels (FIG. 1A-C). The treatment of compound of formula (Ia) increased hemoglobin, RBC and HCT levels by 36.4±6.2, 44.2±10.4, and 37.7±5.7%, respectively, when compared with PHZ control. The PHZ treatment increased serum iron levels, which were decreased by compound of formula (Ia) treatment by 26.0±7.6% (FIG. 1D).

Effect of Compound of Formula (Ia) Treatment in on ROS and TBARS

Treatment of compound of formula (Ia) decreased ROS (DCF concentration) to 9.6±8.9, 25.5±3.8 and 35.1±1.7% at 0.05, 0.5 and 5 μM concentration, respectively, when compared with vehicle control (FIG. 2A). The TBARS levels were decreased to 5.5±4.0, 21.8±4.0 and 27.3±4.0%, at 0.05, 0.5 and 5 μM compound of formula (Ia) concentration, respectively, when compared with vehicle control (FIG. 2B).

Effect of Compound of Formula (Ia) Treatment in on % Erythroid Progenitor Cells

Compound of formula (Ia) treatment increased % erythroid progenitor cells by 2.2±0.5-fold, when compared with vehicle control FIG. 3.

References

Griffiths C. E. M., Barker J. N. W. N. 2007. Pathogenesis and clinical features of psoriasis. Lancet. 370: 263-71.

Tesmer, L. A., Lundy, S. K., Sarkar, S., Fox, D. A., 2008. Th17 cells in human disease. Immunol. Rev. 223, 87-113.

Turbeville, J. G., Patel, N. U., Cardwell, L. A., Oussedik, E., Feldman, S. R., 2017. Recent Advances in Small Molecule and Biological Therapeutic Approaches in the Treatment of Psoriasis. Clin. Pharmacol. Ther. 102, 70-85.

Helliwell P. S., Taylor W. J. 2005. Classification and diagnostic criteria for psoriatic arthritis. Ann Rheum Dis 2005; 64: ii3-ii8.

Dang, E. V., Barbi, J., Yang, H. Y., Jinasena, D., Yu, H., Zheng, Y., Bordman, Z., Fu, J., Kim, Y., Yen, H. R., Luo, W., Zeller, K., Shimoda, L., Topalian, S. L., Semenza, G. L., Dang, C. V., Pardoll, D. M., Pan, F., 2011. Control of TH17/Treg balance by hypoxia-inducible factor 1. Cell 146, 772-784.

McNamee, E. N., Korns Johnson, D., Homann, D., Clambey, E. T., 2013. Hypoxia and hypoxia-inducible factors as regulators of T cell development, differentiation, and function. Immunol. Res. 55, 58-70

Shi, L. Z., Wang, R., Huang, G., Vogel, P., Neale, G., Green, D. R., Chi, H., 2011. HIF1α-dependent glycolytic pathway orchestrates a metabolic checkpoint for the differentiation of TH17 and Treg cells. J. Exp. Med. 208, 1367-1376.

Walmsley, S. R., Print, C., Farahi, N., Peyssonnaux, C., Johnson, R. S., Cramer, T., Sobolewski, A., Condliffe, A. M., Cowburn, A. S., Johnson, N., Chilvers, E. R., 2005. Hypoxia-induced neutrophil survival is mediated by HIF-1α-dependent NF-κB activity. J. Exp. Med. 201, 105-115.

ADDIN Mendeley Bibliography CSL_BIBLIOGRAPHY Albina, J. E., Mastrofrancesco, B., Vessella, J. A., Louis, C. A., Henry, W. L., Reichner, J. S., 2001. HIF-1 expression in healing wounds: HIF-1α induction in primary inflammatory cells by TNF-α. Am. J. Physiol. Cell Physiol. 281, C1971-C1977

Blouin, C. C., Page, E. L., Soucy, G. M., Richard, D. E., 2004. Hypoxic gene activation by lipopolysaccharide in macrophages: Implication of hypoxia-inducible factor 1α. Blood. 103, 1124-1130.

Fitzpatrick, S. F., Tambuwala, M. M., Bruning, U., Schaible, B., Scholz, C. C., Byrne, A., O'Connor, A., Gallagher, W. M., Lenihan, C. R., Garvey, J. F., Howell, K., Fallon, P. G., Cummins, E. P., Taylor, C. T., 2011. An Intact Canonical NF-κB Pathway Is Required for Inflammatory Gene Expression in Response to Hypoxia. J. Immunol. 186, 1091-1096.

Scholz, C. C., Cavadas, M. A. S., Tambuwala, M. M., Hams, E., Rodriguez, J., Von Kriegsheim, A., Cotter, P., Bruning, U., Fallon, P. G., Cheong, A., Cummins, E. P., Taylor, C. T., 2013. Regulation of IL-1β induced NF-κB by hydroxylases links key hypoxic and inflammatory signaling pathways. Proc. Natl. Acad. Sci. U.S.A. 110, 18490-18495.

Robinson, A., Keely, S., Karhausen, J., Gerich, M. E., Furuta, G. T., Colgan, S. P., 2008. Mucosal Protection by Hypoxia-Inducible Factor Prolyl Hydroxylase Inhibition. Gastroenterology 134, 145-155.

Tambuwala, M. M., Cummins, E. P., Lenihan, C. R., Kiss, J., Stauch, M., Scholz, C. C., Fraisl, P., Lasitschka, F., Mollenhauer, M., Saunders, S. P., Maxwell, P. H., Carmeliet, P., Fallon, P. G., Schneider, M., Taylor, C. T., 2010. Loss of prolyl hydroxylase-1 protects against colitis through reduced epithelial cell apoptosis and increased barrier function. Gastroenterology 139, 2093-2101.

Manresa, M. C., Smith, L., Casals-Diaz, L., Fagundes, R. R., Brown, E., Radhakrishnan, P., Murphy, S. J., Crifo, B., Strowitzki, M. J., Halligan, D. N., van den Bogaard, E. H., Niehues, H., Schneider, M., Taylor, C. T., Steinhoff, M., 2019. Pharmacologic inhibition of hypoxia-inducible factor (HIF)-hydroxylases ameliorates allergic contact dermatitis. Allergy Eur. J. Allergy Clin. Immunol. 74, 753-766.

Jain, M., Joharapurkar, A., Patel, V., Kshirsagar, S., Sutariya, B., Patel, M., Patel, H., Patel, P. R., 2019. Pharmacological inhibition of prolyl hydroxylase protects against inflammation-induced anaemia via efficient erythropoiesis and hepcidin downregulation. Eur. J. Pharmacol. 843, 113-120.

Joharapurkar, A. A., Pandya, V. B., Patel, V. J., Desai, R. C., Jain, M. R., 2018. Prolyl Hydroxylase Inhibitors: A Breakthrough in the Therapy of Anaemia Associated with Chronic Diseases. J. Med. Chem. 61, 6964-6982

Patel V J, Joharapurkar A A, Kshirsagar S G, Sutariya B K, Patel M S, Patel H M, Pandey D K, Bahekar R H, Jain M R. Coagonist of glucagon-like peptide-1 and glucagon receptors ameliorates kidney injury in murine models of obesity and diabetes mellitus. World Journal of Diabetes. 2018 Jun. 15; 9(6):80.

Joharapurkar A A, Patel V J, Kshirsagar S G, Patel M S, Saysani H H, Jain M R. Prolyl hydroxylase inhibitor desidustat protects against acute and chronic kidney injury by reducing inflammatory cytokines and oxidative stress. Drug Dev Res. 2021 September; 82(6): 852-860.

The invention claimed is:

1. A pharmaceutical composition comprising a compound of formula (Ia) or a pharmaceutically acceptable salt thereof and one or more pharmaceutically acceptable excipients, for treating sickle cell anemia by administration to a patient in need thereof, wherein compound of formula (Ia) is formula (Ia)

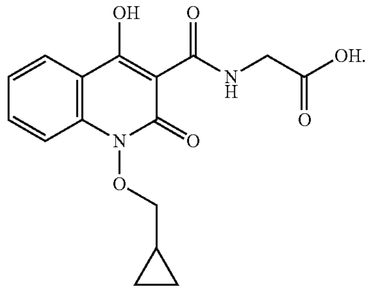

2. The pharmaceutical composition as claimed in claim 1, further comprising a disintegrant and other pharmaceutically acceptable excipients for the treatment of sickle cell anemia.

3. The pharmaceutical composition as claimed in claim 1, configured to deliver from about 1 mg to about 500 mg of the compound of formula (Ia).

4. The pharmaceutical composition as claimed in claim 1, formulated for oral administration.

5. The pharmaceutical composition as claimed in claim 2 wherein the disintegrant is selected from maize starch, sodium starch glycolate, crospovidone, and combinations thereof.

6. The pharmaceutical composition as claimed in claim 2, wherein other pharmaceutically acceptable excipients are selected from the group consisting of diluent, binders, lubricating agents, glidant agents and coating redimix.

7. The pharmaceutical composition as claimed in claim 2, further comprising a diluent selected from the group consisting of lactose monohydrate, lactose, microcrystalline cellulose, polymethacrylates selected from Eudragit, potassium chloride, sulfobutylether b-cyclodextrin, sodium chloride, mannitol, compressible sugars, hydroxylpropyl cellulose, magnesium carbonate, calcium carbonate, maltitol, lactitol, sorbitol, sugar alcohol, magnesium oxide, calcium silicate, spray dried lactose, and suitable combinations thereof.

8. The pharmaceutical composition as claimed in claim 2, further comprising a binder selected from the group consisting of hypromellose 3 Cps, carbomers, cellulose derivatives, cellulose acetate phthalate, carbopol, gellan, chitosan, hydrogenated vegetable oil, sodium algenate, povidone, sugar, hydroxypropylmethyl-cellulose, hydroxypropyl cellulose, starch, alginic acid, acacia, pre-gelatinized starch, tragacanth, eudragit, xanthan gum, polymethacrylates and suitable combination thereof.

9. The pharmaceutical composition as claimed in claim 2, further comprising a glidant selected from colloidal silica, fumed silica, calcium silicate, magnesium silicate, silicon hydrogel, cornstarch, talc, bentonite and suitable combinations thereof.

10. The pharmaceutical composition as claimed in claim 2, further comprising a lubricant selected from the group consisting of calcium stearate, magnesium stearate, mineral oil, stearic acid, silica, zinc stearate, glycerin behenate, vegetable oil, hydrogenated vegetable oil, castor oil, hydrogenated castor oil, fats, sodium stearyl fumarate, talc and fatty acids.

11. A method of treating sickle cell anemia in patients in need thereof, comprising administering to the patient a therapeutically effective amount of a compound of formula (Ia) or a pharmaceutically acceptable salt thereof, wherein compound of formula (Ia) is formula (Ia)

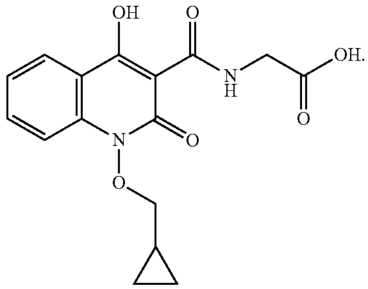

12. The method of claim 11, wherein the therapeutically effective amount is from about 1 mg to about 500 mg.

13. The method of claim 12, wherein the therapeutically effective amount is from about 4 mg to about 50 mg.

14. The method of claim 11, wherein administration is by a route selected from oral, topical, or parenteral administration.

15. The method of claim 14, wherein administration is oral.

16. The method of claim 11, further comprising co-administering at least one additional therapeutic agent selected from hydroxyurea, crizanlizumab, voxelotor, L-glutamine, a non-steroidal anti-inflammatory drug (NSAID), or a prolyl hydroxylase inhibitor.

17. The method of claim 11, wherein treatment results in an increase in hemoglobin.

18. The pharmaceutical composition as claimed in claim 3, configured to deliver from about 4 mg to about 50 mg of the compound of formula (Ia).

* * * * *